(12) United States Patent
Awad

(10) Patent No.: US 12,415,068 B2
(45) Date of Patent: Sep. 16, 2025

(54) LEADLESS PACEMAKER DEVICE AND METHOD OF USE THEREOF

(71) Applicant: Rush University Medical Center, Chicago, IL (US)

(72) Inventor: Sawsan Awad, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 601 days.

(21) Appl. No.: 17/437,474

(22) PCT Filed: Mar. 12, 2019

(86) PCT No.: PCT/US2019/021806
§ 371 (c)(1),
(2) Date: Sep. 9, 2021

(87) PCT Pub. No.: WO2020/185217
PCT Pub. Date: Sep. 17, 2020

(65) Prior Publication Data
US 2022/0152381 A1    May 19, 2022

(51) Int. Cl.
*A61N 1/37*  (2006.01)
*A61N 1/05*  (2006.01)
*A61N 1/375* (2006.01)
*A61N 1/378* (2006.01)

(52) U.S. Cl.
CPC ............ *A61N 1/057* (2013.01); *A61N 1/059* (2013.01); *A61N 1/3756* (2013.01); *A61N 1/378* (2013.01); *A61N 2001/0578* (2013.01); *A61N 2001/058* (2013.01)

(58) Field of Classification Search
CPC ....... A61N 1/057; A61N 1/059; A61N 1/3756
See application file for complete search history.

(56) References Cited

U.S. PATENT DOCUMENTS

| | | |
|---|---|---|
| 2013/0123875 A1 | 5/2013 | Varady et al. |
| 2014/0296846 A1 | 10/2014 | Huszar et al. |
| 2014/0343348 A1* | 11/2014 | Kaplan ................ A61M 5/158 604/21 |
| 2016/0317825 A1 | 11/2016 | Jacobson |
| 2017/0143955 A1 | 5/2017 | Soltis et al. |
| 2017/0326355 A1* | 11/2017 | Koop ..................... A61B 5/686 |
| 2018/0104452 A1 | 4/2018 | Goodman et al. |
| 2019/0192863 A1* | 6/2019 | Koop ..................... A61N 1/056 |
| 2020/0054882 A1* | 2/2020 | Dale ................... A61N 1/37518 |

OTHER PUBLICATIONS

International Search Report dated May 24, 2019, from corresponding International Application No. PCT/US2019/021806.
(Continued)

*Primary Examiner* — Eric D. Bertram
(74) *Attorney, Agent, or Firm* — Barnes & Thornburg LLP

(57) ABSTRACT

The present invention generally relates to leadless pacemaker devices for facilitating regulation of a patient's heart rate and to methods of implanting and using such devices. In one embodiment, the pacemaker device includes a first and a second expandable structure connected by a neck region. A pacemaker unit is contained within one of the expandable structures and a power source is contained within the other of the expandable structures and is electrically connected to the pacemaker unit.

8 Claims, 9 Drawing Sheets

(56) References Cited

OTHER PUBLICATIONS

International Preliminary Report on Patentability dated Aug. 25, 2021, from corresponding International Application No. PCT/US2019/021806.
Koruth, JS et al. "Feasabilityand Efficacy of Percutaneously Delivered Leadless Cardiac Pacing in an In Vivo Ovine Model". J Cardiovasc Electrophysiol, Mar. 2015, vol. 26, pp. 322-328.
Reddy, VY et al. "Percutaneous Implantation of an Entirely Intracardiac Leadless Pacemakder". The New England Journal of Medicine, 373: 1125-1135.
Reynolds, D et al. "A Leadless Intracardiac Transcatheter Pacing System". The New England Journal of Medicine, Nov. 2015, 373: online.
Link, MS, "Achilles' Lead: Will Pacemakers Break Free?". The New England Journal of Medicine, Feb. 2016, 373: online.
Knops, RE et al. "Chronic Performance of a Leadless Cardiac Pacemaker". The Journal of the American College of Cardiology, Apr. 2015, 65:1497-504.
Gold, M. "Are Leadless Pacemakers a Niche or the Future of Device Therapy?". The Journal of the American College of Cardiology, Apr. 2015, 65:1505-6.

\* cited by examiner

LEADLESS PACEMAKER DEVICE AND METHOD OF USE THEREOF

RELATED APPLICATIONS

This application is a National Stage application of International Application No. PCT/US2019/021806, filed Mar. 12, 2019.

TECHNICAL FIELD

The present invention generally relates to leadless pacemaker devices for facilitating regulation of a patient's heart rate and to methods of implanting and using such devices.

BACKGROUND

A healthy heart automatically regulates its own heart rate in response to the needs of the subject. However, when the heart becomes damaged or diseased, it may beat too slowly or in an irregular pattern.

The preferred method of treatment for such a condition often includes the implantation of a pacemaker or other cardiac rhythm management device. Implantation of a traditional pacemaker requires a surgical incision be made in the chest of the patient and the positioning of the pacemaker in a pocket under the patient's skin. Thin insulated wires are then implanted leading from the pacemaker through the veins and into the heart. When required, these leads deliver electrical pulses that prompt the heart to beat at the required rate.

Although the incidence of complications resulting from this treatment protocol is relatively low, complications do occur and are typically associated with infection within the pocket in the patient's chest where the pacemaker is implanted or with movement of the leads running between the device and the patient's heart. Such complications can have a serious impact on a patient's quality of life and also can be expensive to address. Even if complications do not occur, the patient will have a scar and lump where pacemaker is implanted. There is a need for improved pacemaker devices and for simplified delivery methods for the implantation of such devices.

BRIEF SUMMARY

One aspect of the present invention provides a medical device including a first expandable structure having a first end and a second end and including a battery, a second expandable structure having a first end and a second end and including a pacemaker unit. A neck region extends along a longitudinal axis of the device and attaches the first end of the first expandable structure to the first end of the second expandable structure. The pacemaker unit is electrically connected to the battery.

At least one of the expandable structures may have a circular or oval lateral cross section when expanded. In one embodiment, at least one of the expandable structures includes an expandable metal mesh. The expandable metal mesh may include a nickel-titanium alloy or stainless steel. In another embodiment, the battery attaches to the expandable metal mesh of the first expandable structure.

The device may also include an attachment port at the second end of one of the expandable structures and extending along the longitudinal axis and away from the expandable structures. In another embodiment, the device includes a barb attached to the second end of the other expandable structure and extending longitudinally away from the expandable structures.

The device may also include a sheath attaching to at least one of the expandable structures. In one embodiment, the sheath includes a polymeric material.

In yet another embodiment, the pacemaker unit is electrically connected to the battery through the neck region to the pacemaker unit. The pacemaker may include either a bipolar or a monopolar electrode. There are no wires connecting the device to any other structure or device.

Another aspect of the invention provides a method of placing the device in the wall of a patient's heart. For example, the wall of the device is intimate to the wall of the right ventricle of the heart. In one embodiment, the method including the pacemaker device as disclosed herein to a first side of the wall and advancing the first expandable structure through the wall to a second side of the wall. The first expandable structure is then expanded and positioned against the second side of the wall and the second expandable structure is expanded at the first side of the wall.

The device may be delivered within the lumen of a delivery catheter. In one embodiment, the device is delivered to the inside wall of the right ventricle of the heart through a vascular vessel using a percutaneous delivery method. In other embodiments, the device may be delivered to the outside wall of the right ventricle as part of a hybrid surgical procedure or by a laparoscopic surgical method.

The patient may be a human patient, for example, an adult human patient, a neonate human patient or a pediatric human patient. The device may also be delivered in utero to a third trimester fetus.

DETAILED DESCRIPTION

Figure 1:
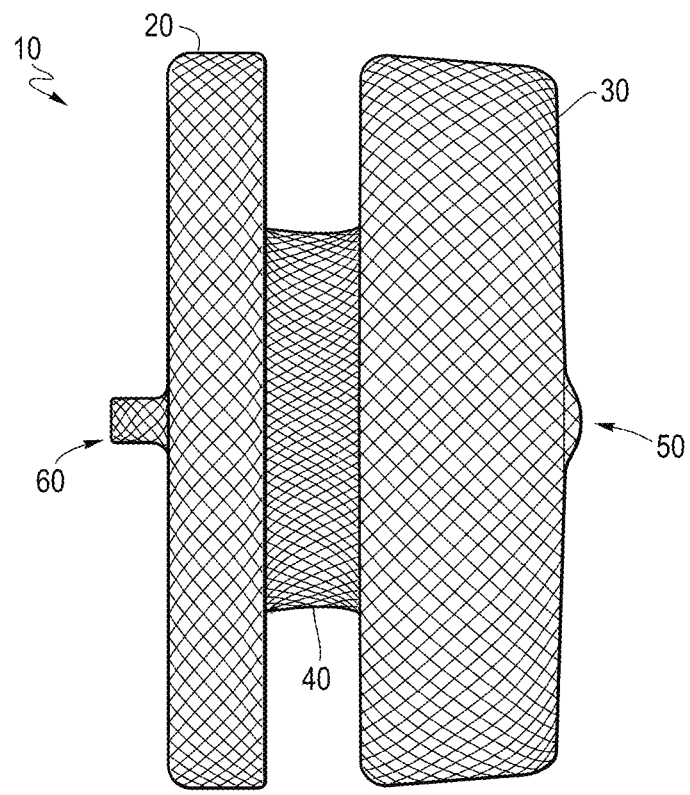
FIG. 1 is a schematic illustration of one embodiment of a device of the present invention. In this illustration, first and second expandable structures are shown to be connected by a neck region and are illustrated in an already expanded state.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Each disclosed feature or features can be combined with the generalized features discussed herein, to form a disclosed embodiment of the present invention.

As used herein, the term "proximal" refers to a portion of the device closest to the operator in the direction of delivery when placing the device in the patient, and the term "distal" refers to a portion of the device furthest away in the direction of delivery and is closest to the end first inserted into the patient's body.

As used herein, the term patient includes a human or a veterinary patient.

Implantable Pacemaker Devices

The present invention provides an implantable pacemaker device suitable for implantation in the wall of the heart of a patient. In one embodiment, the device is a leadless device including both a pacemaker unit and a power source suitable for powering such a unit.

Turning to FIG. 1, there is illustrated a schematic representation of one embodiment of a pacemaker device of the present invention. Device 10 includes proximal expandable structure 20 and distal expandable structure 30. The two expandable structures are connected by neck region 40. Both of the expandable structures are shown in their fully expanded configurations.

In one embodiment of the invention, the proximal end of proximal expandable structure 20 includes connector port 60. As is described in more detail below, connector port 60 may be used to link pacemaker device 10 to the distal end of a delivery cable located within the delivery catheter, to assist in the delivery of the device using a percutaneous or other delivery method. In another embodiment, pacemaker device 10 includes barb 50, or another needle-like structure, for use in penetrating the wall of the heart during the delivery process. In another embodiment, the tip of the delivery catheter will contain a beveled needle that, when unsheathed, will penetrate the wall of the heart to allow passage of the delivery catheter through the ventricular heart. Both of the expandable structures may be collapsed to a small cross-section so as to fit within the lumen of a delivery catheter and, in their expanded configuration, are sufficiently malleable to conform to the curvature of the heart wall and be intimately attached to same.

Figure 2:
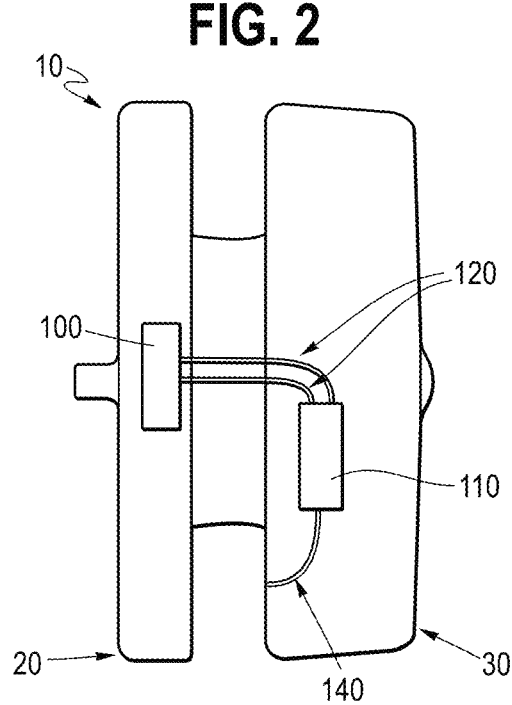
FIG. 2 is a schematic illustration of one embodiment of a device of the present invention showing a pacemaker unit and battery associated with the first and second expandable structures shown in FIG. 1.

Turning now to FIG. 2, there is shown a schematic representation of the placement of pacemaker unit 110 and power source 100. In the embodiment illustrated in FIG. 2, power source 100 is associated with proximal expandable structure 20 and pacemaker unit 110 with distal expandable structure 30. Of course, the present invention also includes embodiments in which the positions of the power source and pacemaker unit are reversed, i.e. where the power source is associated with distal expandable structure 30 and the pacemaker unit with proximal expandable structure 20.

Pacemaker unit 110 is electrically connected to power source by connecting leads 120. In a preferred embodiment, the power source is a battery, for example a lithium battery, lithium-cadmium or a lithium-iodine battery. The battery may also be of a "paper battery" variety imbedded within the mesh of the device. In another embodiment, the pacemaker and the battery are both within nano tubules making up the structural grid of the device. The pacemaker unit contains all of the circuitry necessary to control the pacemaker operations, such as the monitoring of the electrical signals from the heart of the patient and determining when delivery of an electrical pulse is required. This circuitry may include microprocessors (both ROM and RANI), control sensing, output, telemetry, and diagnostic circuits.

The pacemaker unit also includes the components required to generate the electrical pulse and to deliver the pulse to the heart of the patient. The pace maker unit may be a miniaturized pacemaker unit. In addition, the pacemaker unit includes an insulated wire or wires 140 which deliver electrical pulses from a pulse generator component to the heart of the patient. The wire(s) may also transmit electrical signals from the heart to the pacemaker control circuitry. Finally, at least one conducting electrode is located at the end of the wire. This electrode is placed in electrical contact with the heart wall to allow for the delivery of the electrical pulse to the heart when required. The electrode may include a needle-like barb or other fixation component to aid the attachment of the electrode into the wall of the heart.

The pacemaker unit may include a unipolar or a bipolar pacing system. In the monopolar system the stimulating pulse current flows through a single electrode and returns to the device through the patient's body fluid/tissue. In pacemaker units including a bipolar pacing system, the current returns through a second electrode. For example, in a biopolar system, the wire may be a coaxial wire including an inner central wire, separated from an outer wire by an insulating material. In another embodiment, the bipolar system will comprise two separate wires imbedded in the ventricular muscle at least a few mm apart. The preferred system is a bipolar pacing system. Such a bipolar pacing system is normally less susceptible to over-sensing non-cardiac signals.

Proximal expandable structure 20 and distal expandable structure 30, as well as the neck linking region 40, may be manufactured from braided wires formed from, for example, a biocompatible metal or metal alloy or a biocompatible polymer. Both structures are preferably biased towards an expanded state and may be maintained in their unexpanded configuration by, for example, confining the structures within the lumen of a delivery catheter. In certain embodiments, one or both of the structures are formed from metal or metal alloy wires. In one preferred embodiment, the expandable structures are formed by braiding or otherwise interlacing the metal or metal alloy wires. For example, the wires may be formed from a shape-memory alloy, including a nickel-titanium alloy such as NITINOL.

Such shape-memory alloys "remember" their original shape when deformed return to the pre-deformed shape in response to an external stimulus, for example when heated. A collapsed structure formed from such an alloy can be inserted into a patient's vessel while constrained with a lumen of a device such as a delivery catheter. As the body temperature raises the temperature of the alloy it will return to its pre-deformed configuration and will therefore return to an expanded state following removal of the restraining force exerted by the delivery catheter wall.

In other embodiments, the expandable structures may be formed from another metal or metal alloy, such as stainless steel. Such a material may be "spring-loaded" or biased to the expanded configuration and, when released from a constraining force, will take up its expanded configuration.

Alternatively, the expandable structures may be formed from a biocompatible polymer that has the ability to return from a deformed state to its original shape upon the application of an external stimulus, such as a temperature change. Examples of such shape-memory polymers include block copolymer of polyethylene terephthalate (PET) and polyethyleneoxide (PEO), block copolymers containing polystyrene and poly(1,4-butadiene), and a triblock copolymer made from poly(2-methyl-2-oxazoline) and polytetrahydrofuran.

The battery and the pacemaker unit may be attached to the expandable structures by, for example, the application of a biocompatible adhesive or solder. These components may also be attached using sutures or other filaments. In other embodiments, the battery and/or pacemaker unit may be interweaved within the structure of the expandable structures. In some embodiments, a combination of these attachment methods may be used. In one embodiment, the pacemaker and the battery may be within nano tubules making up the structure of the mesh of the device.

At least one, or more, of the interlaced wires forming the expandable structures and/or neck region may include a radiopaque filler, which can provide for improved X-ray visualization of the pacemaker device during deployment and placement within the wall of the patient's heart. For example, in certain embodiments at least 10, 20, 30, 40, 50, 60, 70, 80, 90 or percentage of the wires include the radiopaque filler.

The fully expanded lateral dimension of the expandable structures may be chosen to provide for secure placement in the wall of the patient's heart. In certain embodiments, at least one of the expandable structures has a maximum fully expanded dimension of between 5 mm and 10 mm, 15 mm, 20 mm, 25 mm or 30 mm. The individual strands can include strands having a cross sectional dimension of, for example, between 0.1 mm and 0.5 mm, or between 0.1 mm and 0.35 mm. The expandable structures may have, but need not have, a similar or identical size. In some embodiments, at least one, or both, of the expandable structures may have a circular or oval lateral cross section when expanded.

At least one of the expandable structures and/or neck region may include a covering of an impermeable fabric, for example, a fabric formed from an impermeable polymeric material, such as a Dacron material. Alternatively, or as well as, an impermeable fabric may be included within one of these components. The fabric may be attached to the expandable structure by a suture or another means of attachment. The presence of such an impermeable material may assist in preventing leakage through the puncture in the heart wall in the vicinity of the device when it is implanted.

Delivery Methods

Another aspect of the present invention provides a method of placing a pacemaker device as disclosed herein in the wall of a patient's heart. In various embodiments, the patient may be, for example, an adult patient, a neonate patient or a pediatric patient. The device may also be delivered in utero to a second or third trimester fetus. In a preferred embodiment, the device is placed with the right ventricle of the heart of the patient, for example at or near the apex of the right ventricle.

Figure 3:
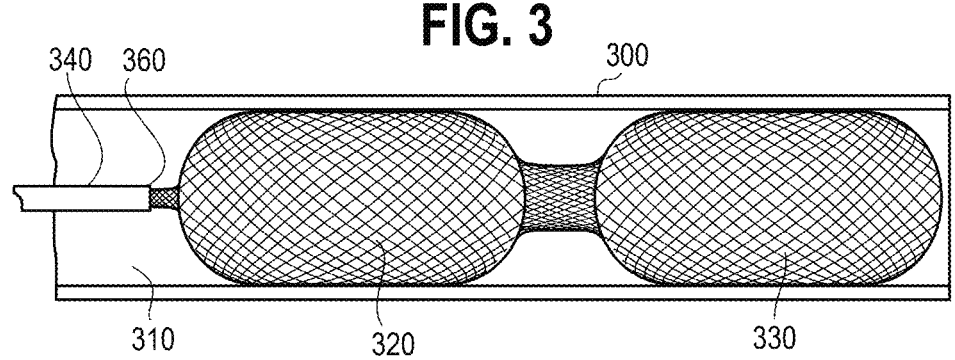
FIG. 3 is a schematic illustration of a device of the present invention. The first and second expandable structures are shown contained in a collapsed state within the lumen of a delivery catheter.
Figure 4:
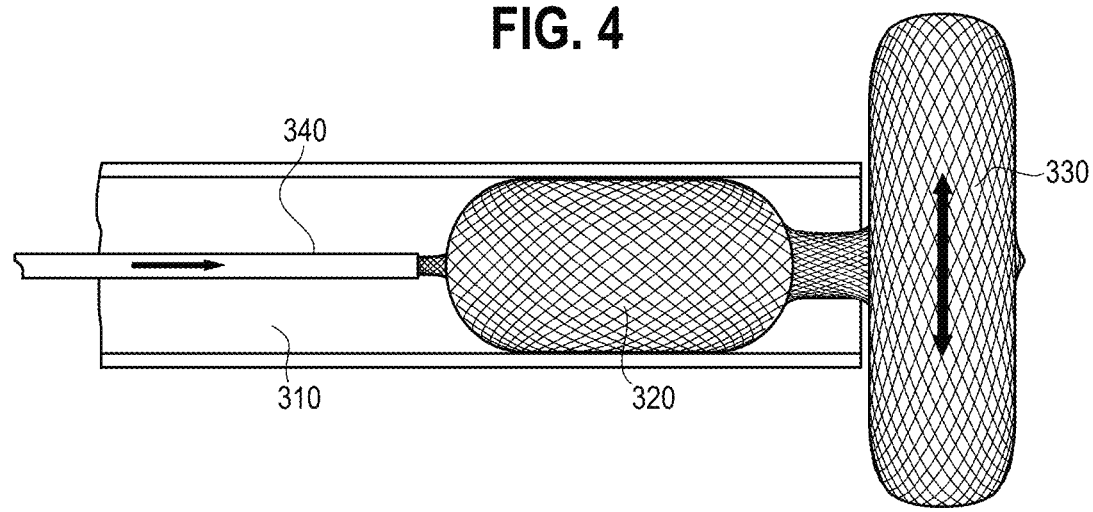
FIG. 4 is another schematic illustration of a device of the present invention. Here, the distal expandable structure is shown in an expanded state after release from the catheter. The proximal expandable structures are shown still contained in a collapsed state within the lumen of the catheter.
Figure 5:
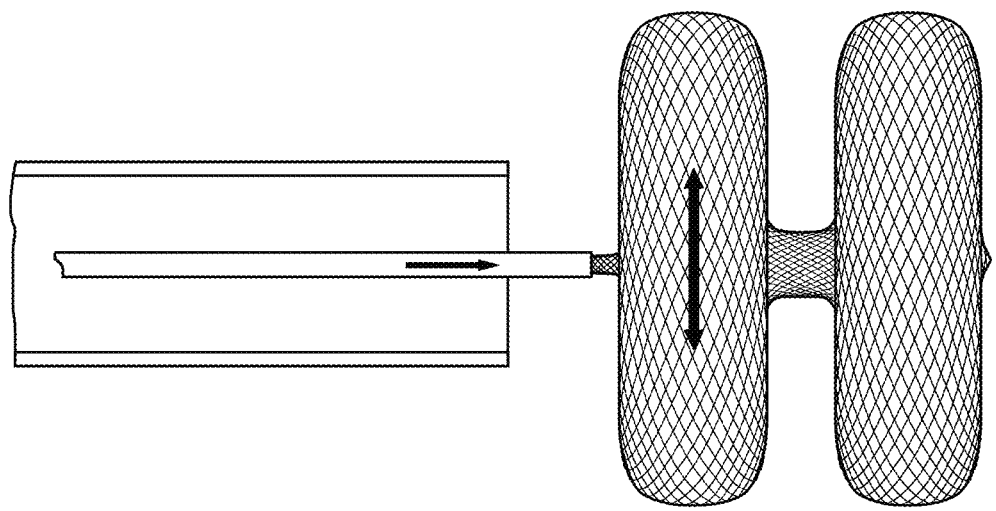
FIG. 5 is yet another schematic illustration of a device of the present invention. Here, the distal and proximal expandable structures are shown in their expanded states after release from the delivery catheter, but still connected to the delivery cable.

Turning now to FIGS. 3 to 5, there are shown schematic illustrations of a method of releasing the pacemaker device from the lumen 310 of delivery catheter 300. FIG. 3 illustrates the distal expandable structure 330 and the distal expandable structure 320 of a pacemaker device as disclosed herein confined in their collapsed configuration within the lumen 310 of delivery catheter 300. Connector port 360 of proximal expandable structure 320 is shown coupled to the distal end of delivery cable 340. The coupling connection may be, for example, a simple male/female screw connection. However, other connection mechanisms may be employed. For example, the distal end of delivery cable 340 may be clamped to connector port 360. All that is required is that the pacemaker device is attached securely to the distal end of delivery cable 340 during the delivery of the device to the wall of the patient's heart and that the device may be detached from the cable after it is inserted into the wall of the patient's heart.

In one embodiment, the wall of the delivery catheter 300 and/or delivery cable 340 is sufficiently rigid to allow the operator to manipulate the catheter and direct it into the right ventricle. For example, these members may be formed from a stiff polymer material, for example, polycarbonate, nylon, polyvinyl or polyethylene terephthalate. In other embodiments, delivery cable 340 is formed of a metal, such as stainless steel or a nickel-titanium shape-memory alloy In other embodiments, the wall of delivery catheter 300 is reinforced along at least a portion of its length. The reinforcement may be a metallic reinforcement formed from, for example, stainless steel or a nickel-titanium shape-memory alloy, such as NITINOL. For example, the metallic reinforcement may be in the form of a metallic coil, a braid or a solid reinforcement. In some embodiments, the reinforcement is at least partially imbedded within polymeric material forming the wall of the delivery catheter.

In one embodiment, reinforcement of the catheter wall may allow for a reduction in the thickness of the wall of the delivery catheter. In various embodiments, the thickness of the wall along at least a portion of the delivery catheter is between 2 mm and 0.5 mm, or 1.5 mm and 0.5 mm or 1.0 mm and 0.5 mm or 2 mm and 1.0 mm or 0.25 mm and 0.5 mm, or 0.25 mm and 0.4 mm, or 0.25 mm and 0.3 mm.

Turning now to FIG. 4. Here, distal expandable structure 330 is shown after release from the lumen 310 of delivery catheter 300 and expansion to its fully expanded configuration. Proximal expandable structure 320 is shown still in its collapsed state, confined within lumen 310. Expandable structure 330 may be released from the lumen either by holding the proximal end of delivery catheter 300 in place and advancing delivery cable 340 and the attached pacemaker device distally or by holding delivery cable 340 in place and withdrawing delivery catheter 300 proximally.

Further advancement of the pacemaker device in a distal direction relative to delivery catheter 300 will eventually result in the release and expansion of proximal expandable structure 320. FIG. 5 shows the pacemaker device with both expandable structures fully expanded after release from delivery catheter 300. Connector port 360 is shown still attached to the distal end of delivery cable 340. After the pacemaker device is positioned within the wall of the patient's heart, delivery cable 340 may be disconnected from connector port 360. For example, where the connection is by way of a screw connector, delivery cable may be rotated with respect to the pacemaker device to unscrew the cable from the pacemaker device.

Figure 6:
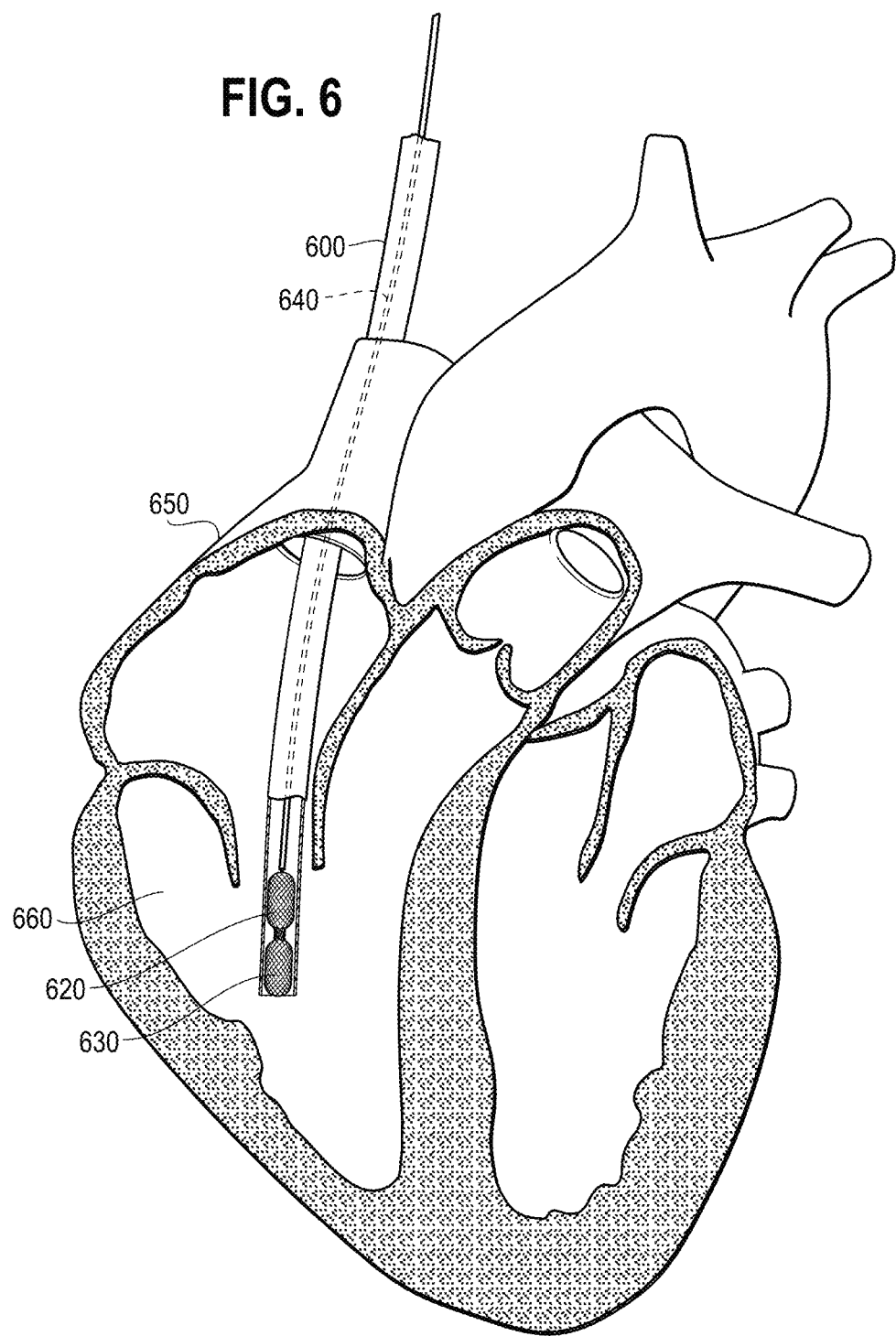
FIG. 6 is a schematic illustration of a device of the present invention during delivery to the right ventricle of the heart while contained within the lumen of a delivery catheter.

One embodiment of a method for inserting the pacemaker device in the wall of a patient's heart will now be disclosed with reference to FIGS. 6-9. Turning first to FIG. 6, a pacemaker device as disclosed herein is delivered to the right ventricle of a patient's heart using a percutaneous delivery technique. Here, the device including proximal expandable structure 620 and distal expandable structure 630 is contained within the lumen of delivery catheter 600. The distal end of the delivery catheter is shown to be positioned within the right ventricle of the heart 650.

In one embodiment, access to the right ventricle is achieved following percutaneous puncture of the femoral vein or the jugular vein. This technique typically involves placing a needle through the skin and into the femoral vein or into the jugular vein. This is followed by introduction of a flexible introducer guide wire to define the pathway through the skin and into the lumen of the vein. The needle is then exchanged for an introducer sheath. The introducer guide wire is then removed and exchanged for the delivery catheter used to deliver the pacemaker device through the right atrium and through the tricuspid valve to the right ventricle of the heart. Typically, the device or the delivery catheter includes a radiopaque filler, to allow the procedure to be guided by a X-ray visualization technique.

Figure 7:
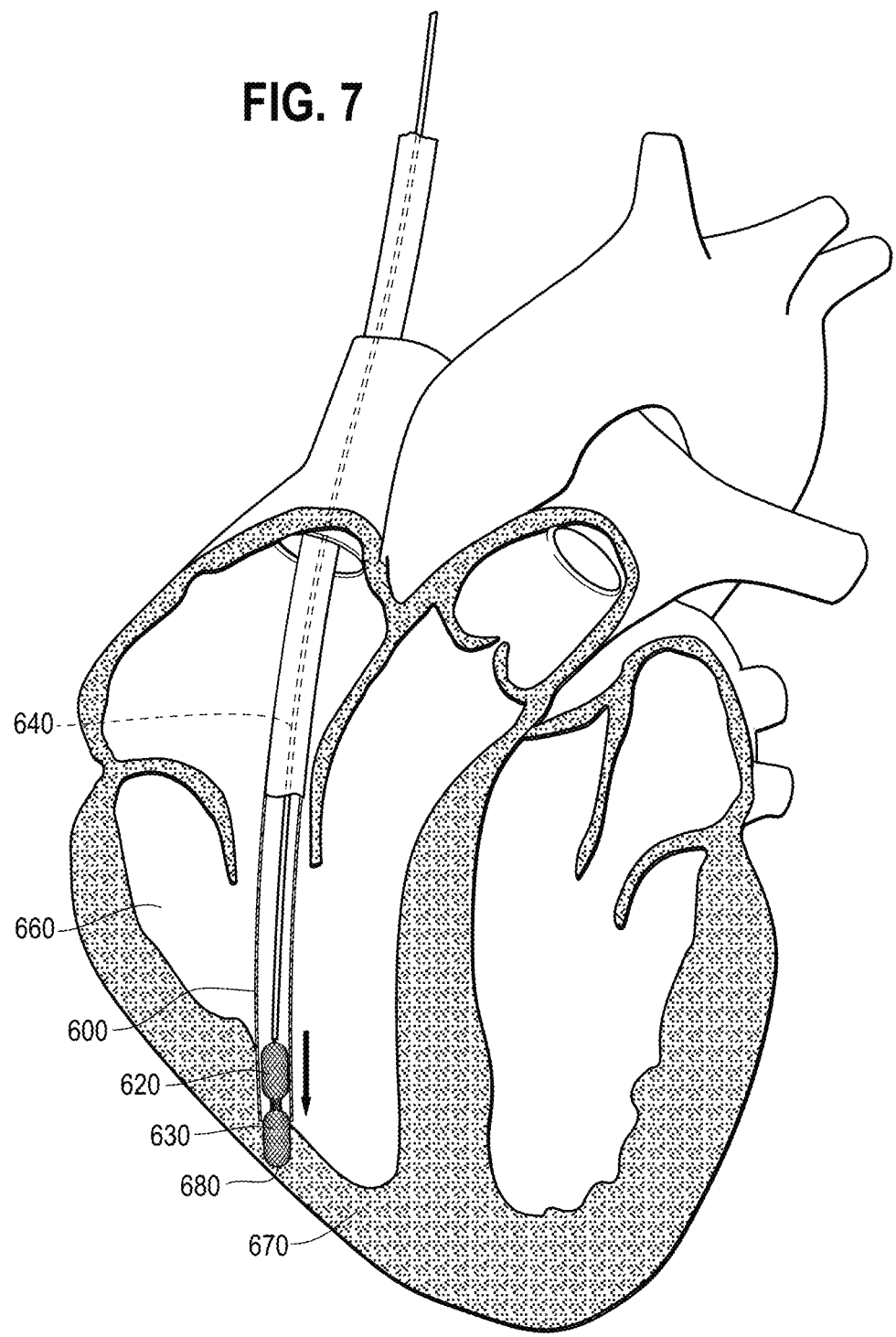
FIG. 7 is a schematic illustration of a device of the present invention during insertion into the wall of the right ventricle of the heart.

Turning now to FIG. 7, here the distal end of delivery catheter 600 is shown to be inserted into the wall of the heart near the apex region 670 of right ventricle. Typically, the pacemaker device will be positioned in this region of the heart. However, in other embodiments, the device may be positioned in another region of the right ventricle.

In some embodiments the distal end of distal expandable structure 630 includes barb or similar needle-like structure 680 to assist in the puncture of the wall. Alternatively, or as well as, the distal end of delivery catheter 600 may include a structure such a beveled needle that punctures through the heart wall to allow passage of the delivery catheter. In any case, the distal end of the delivery catheter is advanced through the wall and exits through the other side of the wall.

Figure 8:
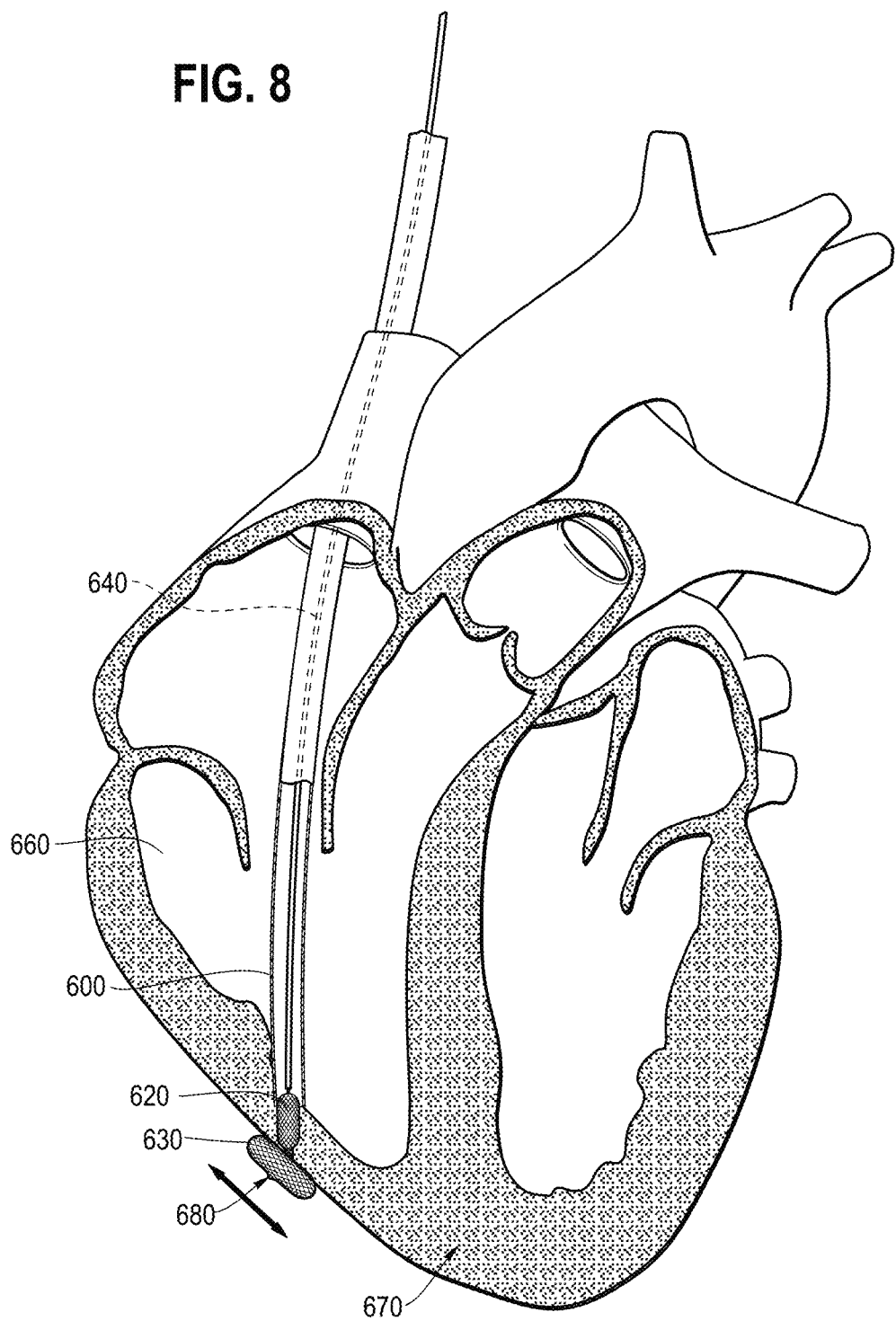
FIG. 8 is a schematic illustration of a device of the present invention with the delivery catheter through the wall of the right ventricle and the distal device expanded and the proximal device still in collapsed form within the delivery catheter

The distal expandable structure 630 is then released from the lumen of delivery catheter 600 and assumes an expanded configuration. FIG. 8 shows the delivery catheter 600 positioned through the ventricular wall with the distal expandable structure 630 expanded outside the wall. The proximal end of expandable structure 630 is positioned against the outside wall of the heart and delivery catheter 600 withdrawn proximally to eventually release proximal expandable structure 620 from the catheter lumen. The distal end of delivery cable 640 is then released from the device and delivery catheter 600 removed from the patient's body.

Figure 9:
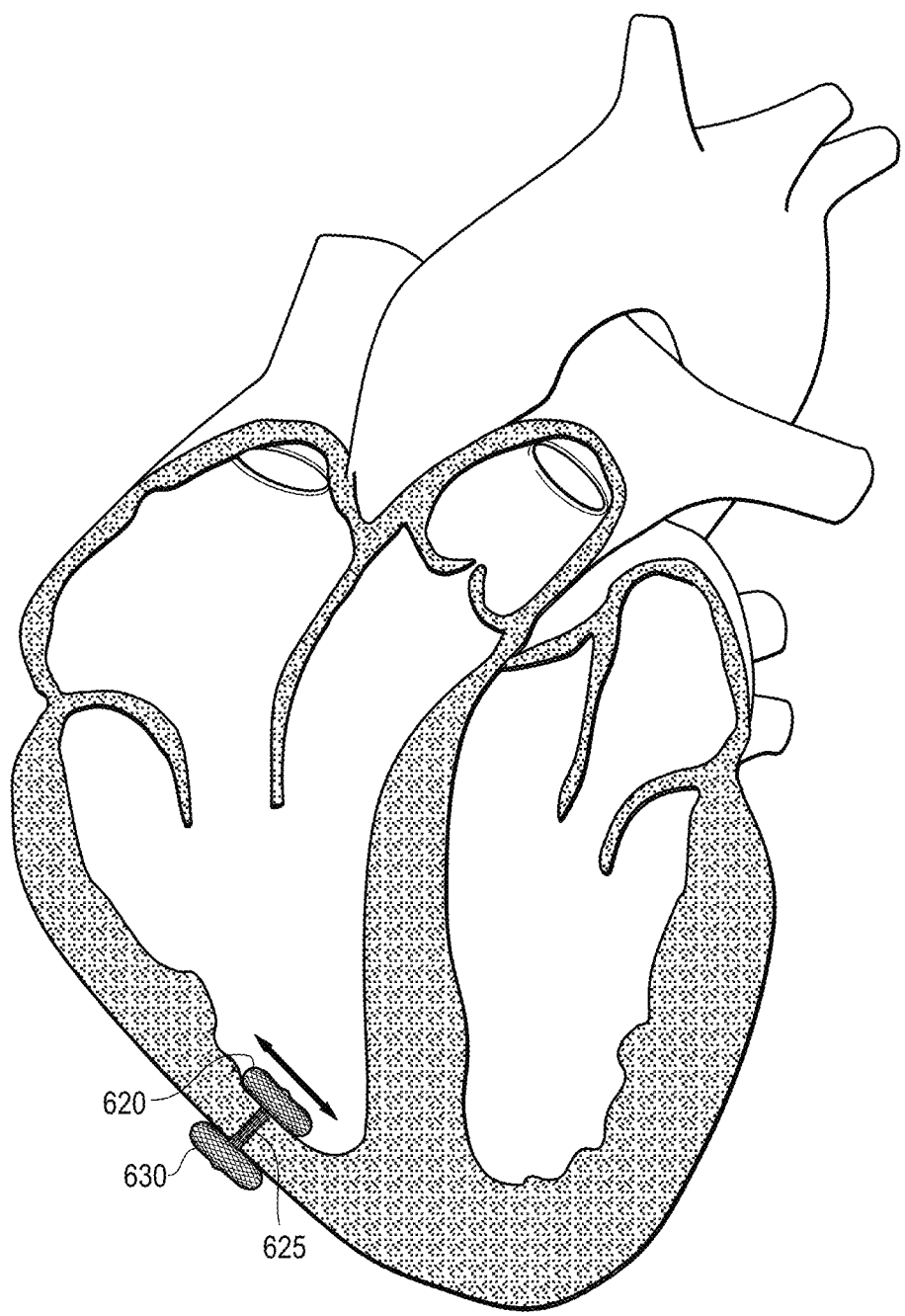
FIG. 9 is a schematic illustration of a device of the present invention in its implanted position in the wall of the right ventricle of the heart.

FIG. 9 illustrates the pacemaker in position in the wall of the heart in the region of the apex of the right ventricle. Here, distal expandable structure 630 is positioned against the outside wall of the heart and proximal expandable structure 620 against the inside wall of the right ventricle. The device is firmly fixed in position by the expanded structures and held together with the neck region 625. Because of the tightness of the approximation of the two expanded devices and the large area of coaptation, the chance of embolization is minuscule. Traditional leadless pacemaker systems are bulky, have a small area of attachment to the ventricular wall and therefore are more susceptible to embolization In one embodiment, the pacemaker electrodes are incorporated into the proximal expandable structure 620. There will be no need to deliver additional devices/electrodes. If the pacemaker unit is positioned in the distal expandable structure, the electrode(s) may be positioned to extend slightly out of the proximal end of the expanded distal structure and may be positioned within the wall by pulling the delivery cable 640 proximally to press the electrode(s) against the surface of the wall. Alternatively, if the pacemaker unit is positioned in the proximal expandable structure, the electrode(s) may be positioned within the wall by the expansion of the proximal expandable structure against the inside wall of the right ventricle.

In another embodiment, the pacemaker device is first delivered to the outside wall of the heart, either by a conventional, hybrid or a laparoscopic surgical method. This method may include the use of a delivery catheter system as is disclosed herein. Delivery of the pacemaker device from the outside of the heart may be the preferred method for in utero delivery, for the delivery to neonates and in other situations where the delivery through the vascular system is difficult due to the small dimensions of the vascular vessels.

Figure 10:
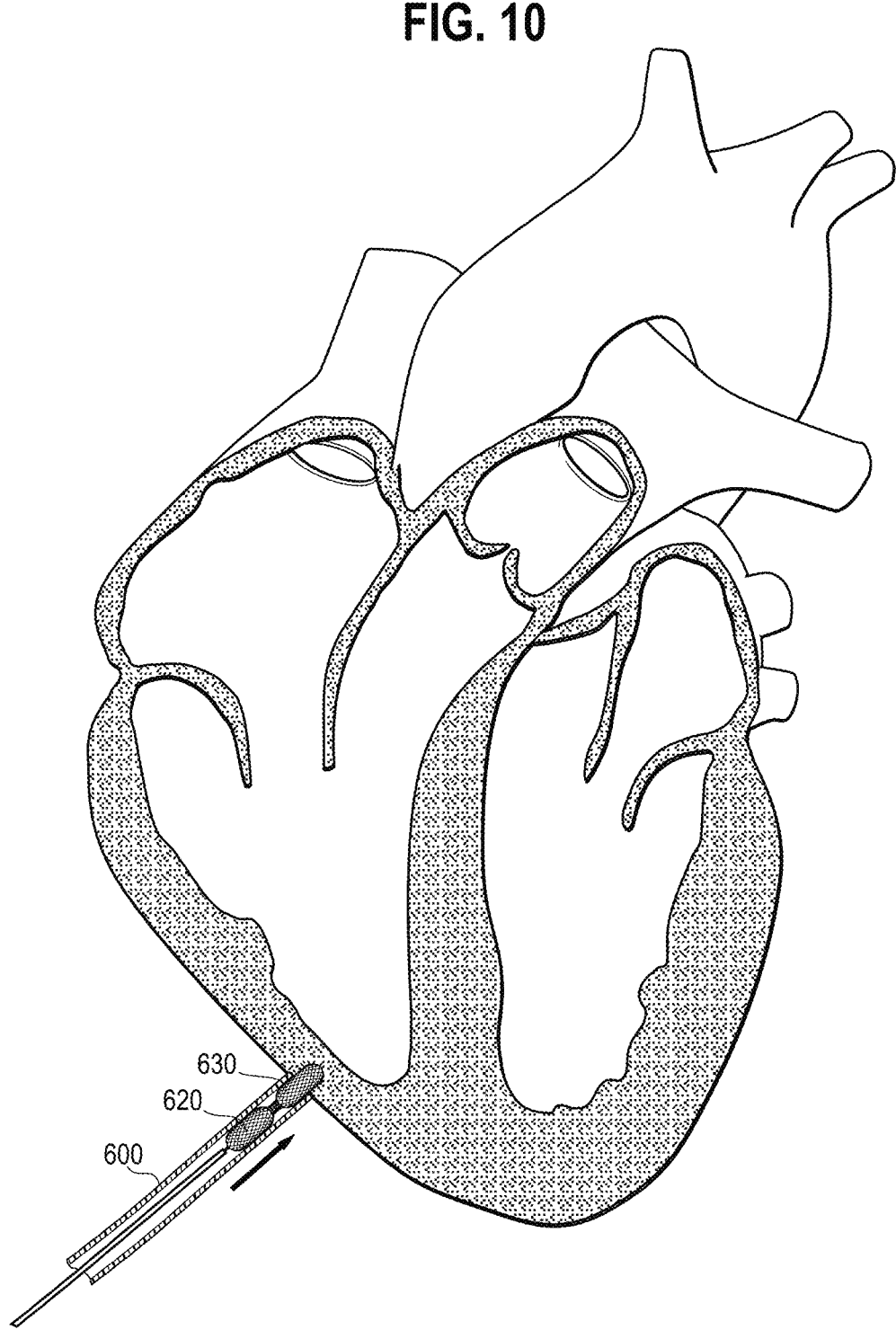
FIG. 10 is a schematic illustration of a device of the present invention during insertion through the external wall of the right ventricle of the heart.
Figure 11:
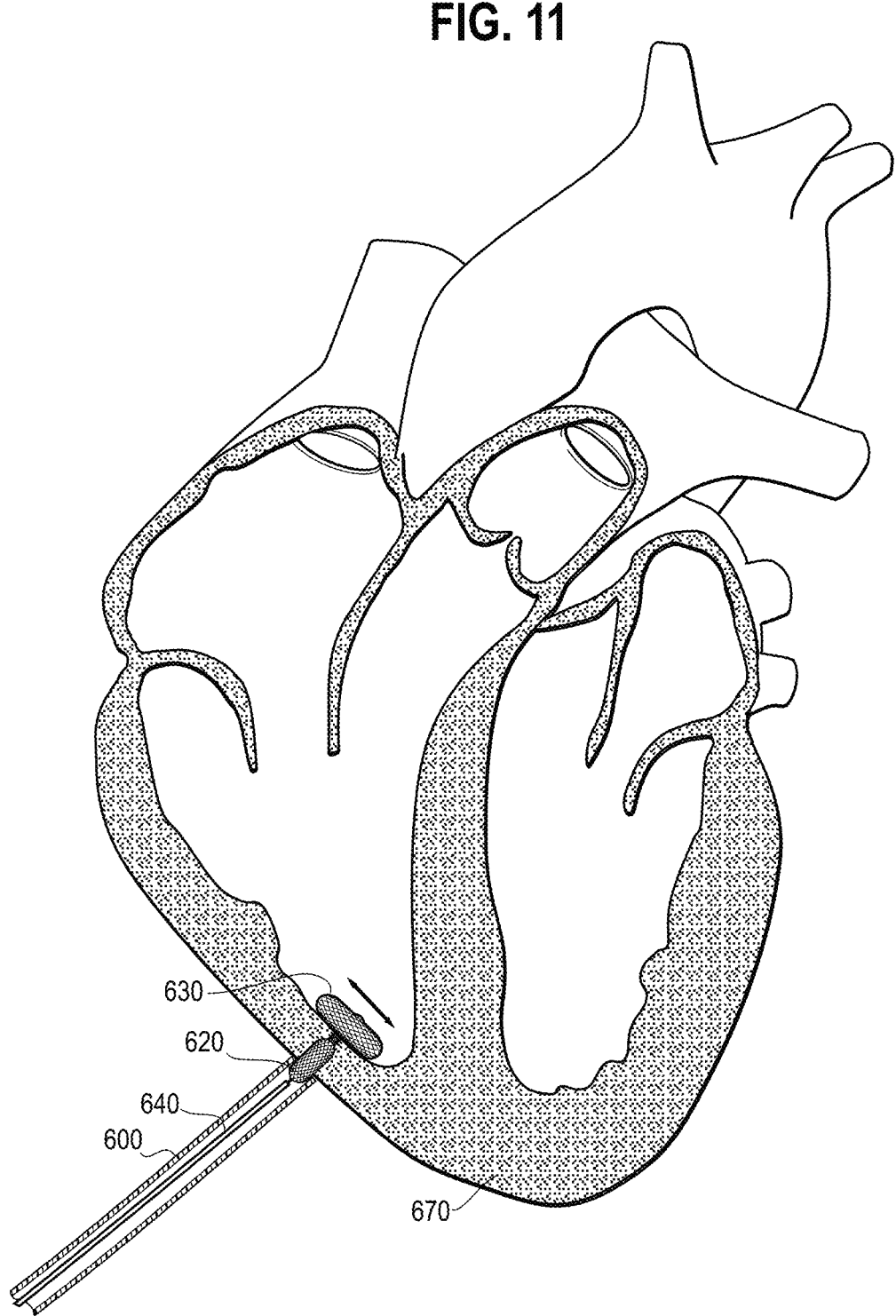
FIG. 11 is a schematic illustration of a device of the present invention after insertion through the external wall of the right ventricle of the heart.
Figure 12:
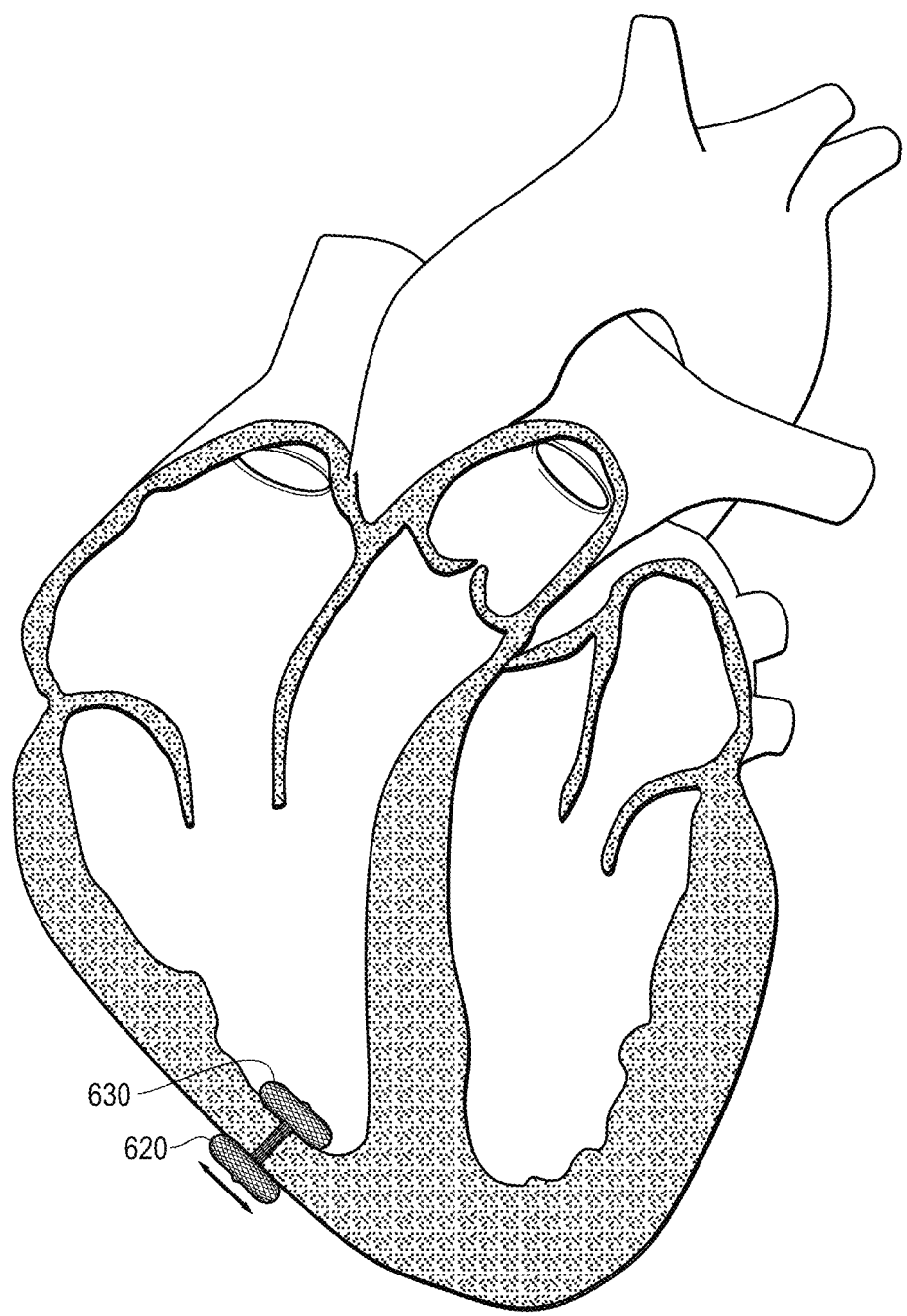
FIG. 12 is a schematic illustration of a device of the present invention positioned in the wall of the right ventricle of the heart.

One embodiment of a method for delivering the pacemaker device into a patient's heart from the outside wall of the right ventricle of the heart will now be disclosed with reference to FIGS. 10-12. In this embodiment, the device is delivered within the lumen of a delivery catheter. Turning first to FIG. 10, a pacemaker device as disclosed herein is delivered to the outside wall of the right ventricle of a patient's heart using, for example, a percutaneous delivery technique. Here, the device including proximal expandable structure 620 and distal expandable structure 630 is contained within the lumen of delivery catheter 600. The distal end of the delivery catheter is shown to be positioned just within the external wall of the right ventricle of the heart.

Turning now to FIG. 11, here the distal end of delivery catheter 600 is shown to be inserted through the wall of the heart near the apex region 670 of right ventricle. Distal expandable structure 630 is expanded and positioned against the inside wall of the right ventricle while proximal expandable structure 620 is still in its collapsed configuration within the delivery catheter.

Delivery catheter 600 may then be withdrawn proximally to eventually release proximal expandable structure 620 from the catheter lumen. The distal end of delivery cable 640 is then released from the device and delivery catheter 600 removed from the patient's body. FIG. 12 illustrates the pacemaker in position in the wall of the heart in the region of the apex of the right ventricle after removal of delivery catheter. Here, distal expandable structure 630 is positioned against the inside wall of the heart and proximal expandable structure 620 against the outside wall of the right ventricle.

Although the invention has been described and illustrated herein with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A method of placing a device to a wall of a patient's heart, the method comprising,
   delivering the device to a first side of the wall of the heart, wherein the device comprises,
      a first expandable structure having a first end and a second end;
      a second expandable structure having a first end and a second end; wherein one of the first expandable structure and the second expandable structure comprises a battery and another of the first expandable structure and the second expandable structure comprises a pacemaker unit; and
      a neck region extending along an longitudinal axis of the device and attaching the first end of the first expandable structure to the first end of the second expandable structure, wherein the pacemaker unit is electrically connected to the battery and wherein the first and second expandable structures are delivered in a collapsed configuration;
   advancing the second end of the first expandable structure through the wall to a second side of the wall;
   expanding the first expandable structure;
   positioning the first end of the first expandable structure against the second side of the wall; and
   expanding the second expandable structure at the first side of the wall.

2. The method of claim 1, wherein the device is delivered to the first side of the wall within a lumen of a delivery catheter.

3. The method of claim 1, wherein the device is delivered to an inside wall of the right ventricle.

4. The method of claim 3, wherein the device is delivered by an open heart surgical procedure or through a vascular vessel by a percutaneous delivery method.

5. The method of claim 1, wherein the device is delivered by a laparoscopic surgical method.

6. The method of claim 1, wherein the pacemaker unit is positioned against the inside wall of the right ventricle.

7. The method of claim 1, therein the patient is a human patient selected from the group consisting of a third trimester fetus, a neonate patient, a pediatric patient and an adult patient.

8. A device comprising:
   a first expandable structure having a first end and a second end and comprising a battery;
   a second expandable structure having a first end and a second end and comprising a pacemaker unit,
   a neck region extending along a longitudinal axis of the device and attaching the first end of the first expandable structure to the first end of the second expandable structure;
   wherein the pacemaker unit is electrically connected to the battery, and wherein the first expandable structure, second expandable structure, and neck region are formed from braided wires.

* * * * *